United States Patent
Ohishi

(10) Patent No.: US 10,229,515 B2
(45) Date of Patent: Mar. 12, 2019

(54) RADIATION DIAGNOSIS APPARATUS

(71) Applicant: Toshiba Medical Systems Corporation, Otawara-shi (JP)

(72) Inventor: Satoru Ohishi, Otawara (JP)

(73) Assignee: Toshiba Medical Systems Corporation, Otawara-shi (JP)

(*) Notice: Subject to any disclaimer, the term of this patent is extended or adjusted under 35 U.S.C. 154(b) by 78 days.

(21) Appl. No.: 15/012,198

(22) Filed: Feb. 1, 2016

(65) Prior Publication Data
US 2016/0232661 A1 Aug. 11, 2016

(30) Foreign Application Priority Data
Feb. 10, 2015 (JP) .................. 2015-024728

(51) Int. Cl.
G06T 11/00 (2006.01)
A61B 6/03 (2006.01)
A61B 6/00 (2006.01)

(52) U.S. Cl.
CPC .......... *G06T 11/003* (2013.01); *A61B 6/032* (2013.01); *A61B 6/037* (2013.01); *A61B 6/481* (2013.01); *A61B 6/504* (2013.01); *A61B 6/5205* (2013.01); *A61B 6/501* (2013.01); *G06T 2207/30016* (2013.01); *G06T 2207/30101* (2013.01); *G06T 2207/30104* (2013.01)

(58) Field of Classification Search
None
See application file for complete search history.

(56) References Cited

U.S. PATENT DOCUMENTS 6,442,228 B1 * 8/2002 Woloschek ............ A61B 6/032
378/8
7,983,465 B2 * 7/2011 Leroux ................. G06T 11/006
250/363.04
(Continued)

FOREIGN PATENT DOCUMENTS

JP 2007-229254 A 9/2007
JP 2013-526365 A 6/2013
(Continued)

OTHER PUBLICATIONS

He, L., Orten, B., Do, S., Karl, W.C., Kambadakone, A., Sahani, D.V. and Pien, H., 2010. A spatio-temporal deconvolution method to improve perfusion CT quantification. IEEE Transactions on Medical Imaging, 29(5), pp. 1182-1191.*
(Continued)

*Primary Examiner* — Michelle M Entezari
(74) *Attorney, Agent, or Firm* — Oblon, McClelland, Maier & Neustadt, L.L.P.

(57) ABSTRACT

A radiation diagnosis apparatus according to an embodiment includes reconstructing circuitry. The reconstructing circuitry reconstructs three-dimensional medical agent distribution images in a time series from a group of acquired images acquired in the presence of a medical agent by an imaging system from directions in a range that makes it possible to reconstruct three-dimensional images of a subject, by performing an iterative reconstruction process that uses at least one selected from between spatial continuity of the medical agent and temporal continuity of the concentration of the medical agent as a constraint condition.

16 Claims, 9 Drawing Sheets

(56) References Cited

U.S. PATENT DOCUMENTS

| | | | | |
|---|---|---|---|---|
| 8,244,331 | B2* | 8/2012 | Deinzer | A61B 6/481 378/21 |
| 8,290,225 | B2* | 10/2012 | Lobregt | A61B 5/055 345/419 |
| 9,761,019 | B2* | 9/2017 | Yu | G06T 11/003 |
| 9,770,223 | B2* | 9/2017 | Samsonov | A61B 6/504 |
| 2003/0144813 | A1* | 7/2003 | Takemoto | G06T 1/0007 702/153 |
| 2008/0292163 | A1* | 11/2008 | DiBella | G01R 33/561 382/131 |
| 2009/0028409 | A1* | 1/2009 | Tsukagoshi | A61B 6/032 382/131 |
| 2010/0014730 | A1* | 1/2010 | Hahn | G06T 5/50 382/131 |
| 2011/0038517 | A1* | 2/2011 | Mistretta | A61B 6/02 382/128 |
| 2012/0256092 | A1* | 10/2012 | Zingerman | A61B 6/032 250/363.03 |
| 2014/0153803 | A1 | 6/2014 | Noda | |
| 2015/0173699 | A1* | 6/2015 | Kyriakou | A61B 6/466 378/62 |
| 2015/0238159 | A1* | 8/2015 | Al Assad | A61B 6/5258 378/5 |

FOREIGN PATENT DOCUMENTS

| | | |
|---|---|---|
| JP | 2014-128576 | 7/2014 |
| JP | 2014128648 A | 7/2014 |
| JP | 2014-195492 A | 10/2014 |

OTHER PUBLICATIONS

Satoru Ohishi et al. "Reconstruction of blood vessels from an insufficient number of projections obtained from venography", Optics Communications, vol. 102, 1993, 7 Pages.

Office Action dated Dec. 4, 2018 in Japanese Patent Application No. 2015-024728.

* cited by examiner

FIG.3
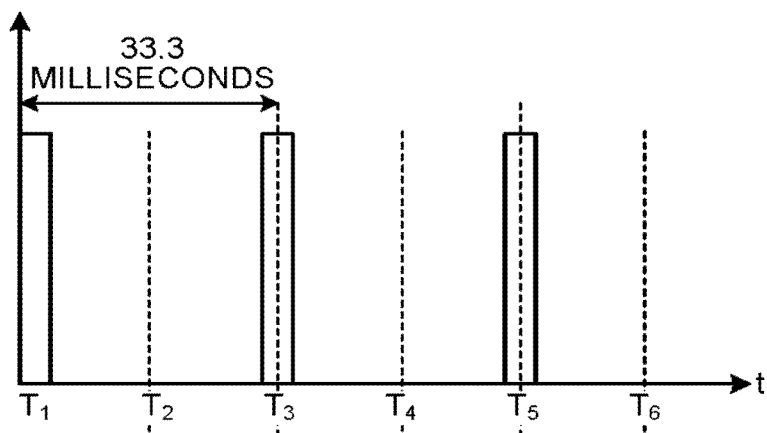
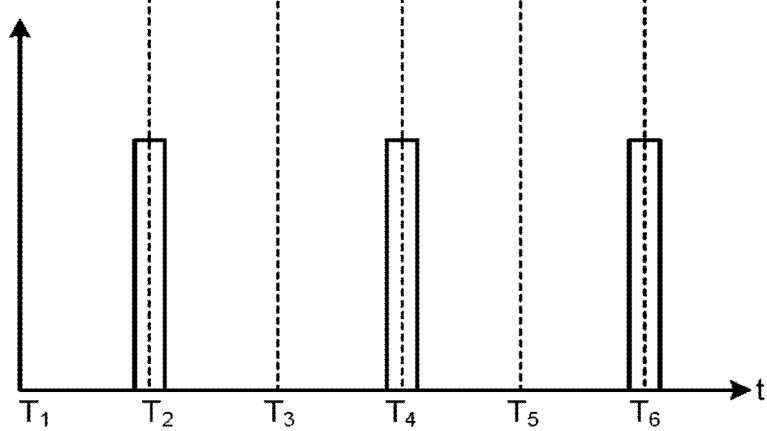

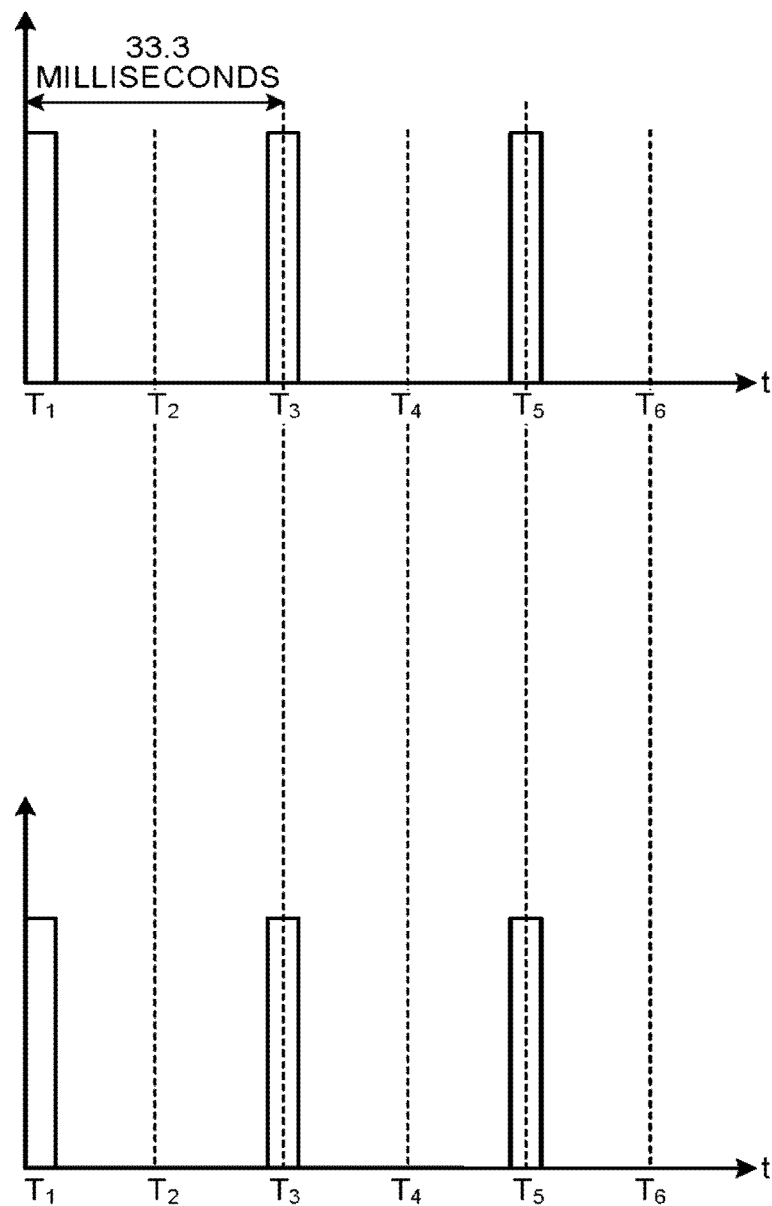

RADIATION DIAGNOSIS APPARATUS

CROSS-REFERENCE TO RELATED APPLICATIONS

This application is based upon and claims the benefit of priority from Japanese Patent Application No. 2015-024728, filed on Feb. 10, 2015, the entire contents of all of which are incorporated herein by reference.

FIELD

Embodiments described herein relate generally to a radiation diagnosis apparatus.

BACKGROUND

It is possible to diagnose subarachnoid hemorrhage through a CT-like imaging process performed by using an X-ray diagnosis apparatus. In contrast, it is difficult to diagnose cerebral infarction through a CT-like imaging process performed by using an X-ray diagnosis apparatus and a contrast agent. For this reason, to diagnose cerebral infarction, a perfusion process is performed by using an X-ray Computed Tomography (CT) apparatus and a contrast agent. In the following sections, the perfusion process performed by using an X-ray CT apparatus and a contrast agent will be referred to as a CTP process as appropriate. During the CTP process, three-dimensional blood vessel images in a time series are reconstructed so as to use the reconstructed images for diagnosing cerebral infarction.

BRIEF DESCRIPTION OF THE DRAWINGS

FIG. 3 is a first drawing for explaining the first embodiment;

FIG. 6 is a drawing for explaining a modification example of the first embodiment;

DETAILED DESCRIPTION

A radiation diagnosis apparatus according to an embodiment includes reconstructing circuitry. The reconstructing circuitry reconstructs three-dimensional medical agent distribution images in a time series from a group of acquired images acquired in the presence of a medical agent by an imaging system from directions in a range that makes it possible to reconstruct three-dimensional images of a subject, by performing an iterative reconstruction process that uses at least one selected from between spatial continuity of the medical agent and temporal continuity of the concentration of the medical agent as a constraint condition.

Exemplary embodiments of a radiation diagnosis apparatus will be explained below, with reference to the accompanying drawings. The radiation diagnosis apparatus according to the exemplary embodiments may be, for example, an X-ray diagnosis apparatus or an X-ray CT apparatus. Possible embodiments, however, are not limited to the embodiments described below. Further, the contents of each of the embodiments are, in principle, similarly applicable to any other embodiments.

First Embodiment

Figure 1:
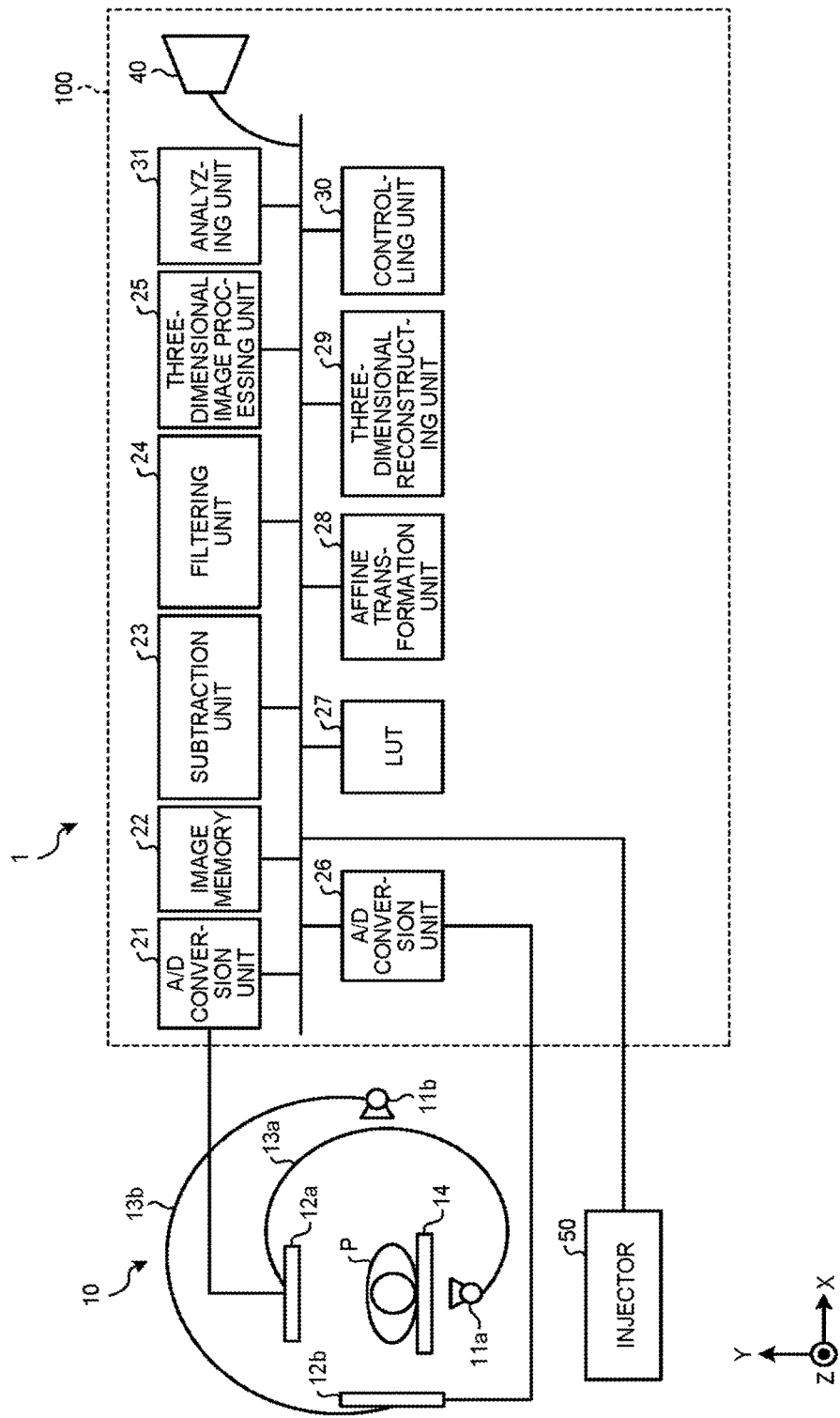
FIG. 1 is a block diagram of an exemplary configuration of an X-ray diagnosis apparatus according to a first embodiment.

In a first embodiment, an X-ray diagnosis apparatus will be explained as an example of the radiation diagnosis apparatus. First, a configuration of an X-ray diagnosis apparatus according to the first embodiment will be explained. FIG. 1 is a block diagram of an exemplary configuration of an X-ray diagnosis apparatus 1 according to the first embodiment. An examined subject (hereinafter, "patient") P (e.g., a human body) is not included in the X-ray diagnosis apparatus 1. The configuration illustrated in FIG. 1 is merely an example. For instance, any of the constituent elements illustrated in FIG. 1 may be configured as being integrated together or as separate, as appropriate.

As illustrated in FIG. 1, the X-ray diagnosis apparatus 1 according to the first embodiment includes an X-ray imaging mechanism 10 and an image processing apparatus 100. The X-ray imaging mechanism 10 is a bi-plane imaging mechanism including a first imaging system and a second imaging system. The first imaging system includes an X-ray tube 11a, an X-ray detector 12a, and a C-shaped arm 13a. The second imaging system includes an X-ray tube 11b, an X-ray detector 12b, and an Ω-shaped arm 13b. In other words, the X-ray imaging mechanism 10 is a bi-plane type imaging system including two sets each made up of an X-ray tube and an X-ray detector.

Further, the X-ray imaging mechanism 10 includes a couch 14 and has an injector 50 connected thereto. The couch 14 is a bed on which the patient P is placed. Further, the X-ray imaging mechanism 10 defines, as illustrated in FIG. 1, a three-dimensional orthogonal coordinate system having an X-axis, a Y-axis, and a Z-axis. In other words, the X-axis expresses the horizontal direction, whereas the Y-axis expresses the vertical direction, and the Z-axis expresses the body-axis direction of the patient P. In the three-dimensional orthogonal coordinate system, the directions indicated with the arrows are the positive directions.

The X-ray tube 11a and the X-ray tube 11b are devices each of which is configured to generate X-rays by using a high voltage supplied thereto from a high-voltage generating unit (not illustrated).

The X-ray detector 12a and the X-ray detector 12b each may be, for example, a Flat Panel Detector (FPD) or an Image Intensifier (I. I.). The X-ray detector 12a and the X-ray detector 12b are devices in each of which X-ray detecting elements configured to detect X-rays that have passed through the patient P are arranged in a matrix formation. The X-ray detecting elements are configured to convert the X-rays that have passed through the patient P into electric signals (X-ray signals), to accumulate the electric signals therein, and to store the accumulated electric signals into an image memory 22 (explained later). The X-ray signals resulting from the conversion by the X-ray detector 12a will be referred to as first X-ray signals. The X-ray signals resulting from the conversion by the X-ray detector 12b will be referred to as second X-ray signals.

The C-shaped arm 13a is an arm configured to hold the X-ray tube 11a and the X-ray detector 12a. The X-ray tube 11a and the X-ray detector 12a are positioned by the C-shaped arm 13a so as to oppose each other while the patient P is interposed therebetween. The C-shaped arm 13a is configured to support the X-ray tube 11a and the X-ray detector 12a and is configured to be rotated at a high speed, like a propeller, around the patient P lying on the couch 14, by a motor provided in a supporting part (not illustrated). In this situation, the C-shaped arm 13a is supported so as to be rotatable with respect to each of the X-, Y-, and Z-axes that are orthogonal to one another and is rotated by a driving unit (not illustrated) on each of the axes individually.

The Ω-shaped arm 13b is an arm configured to hold the X-ray tube 11b and the X-ray detector 12b. The X-ray tube 11b and the X-ray detector 12b are positioned by the Ω-shaped arm 13b so as to oppose each other while the patient P is interposed therebetween. The Ω-shaped arm 13b is configured to support the X-ray tube 11b and the X-ray detector 12b and is configured to be rotated around the patient P lying on the couch 14, by a motor provided in a supporting part (not illustrated) including a ceiling rail. In this situation, the Ω-shaped arm 13b is supported so as to be rotatable with respect to each of the X-, Y-, and Z-axes that are orthogonal to one another and is rotated by a driving unit (not illustrated) on each of the axes individually.

The injector 50 is a device configured to inject a contrast agent through a catheter inserted into the patient P. In this situation, the contrast agent injection from the injector 50 may be started according to an injection start instruction received via the image processing apparatus 100 (explained later) or may be started according to an injection start instruction that is directly input to the injector 50 by an the operator.

The X-ray imaging mechanism 10 configured as described above is controlled by an imaging controlling unit (not illustrated). For example, the imaging controlling unit is configured to control various types of processes related to imaging processes performed by the X-ray imaging mechanism 10, under control of a controlling unit 30 (explained later). For example, the imaging controlling unit controls a rotation imaging process by which projection data is acquired at a predetermined frame rate while the C-shaped arm 13a and the Ω-shaped arm 13b are being rotated. In one example, the imaging controlling unit controls the rotation imaging process performed a plurality of times after a single contrast agent injection, as being triggered by a signal output from the injector 50 when the contrast agent injection is started. Further, while rotation control is exercised over the C-shaped arm 13a and the Ω-shaped arm 13b, the imaging controlling unit controls the high-voltage generating unit (not illustrated) so that X-rays are generated from the X-ray tube 11a and the X-ray tube 11b either continuously or intermittently and so that the X-rays that have passed through the patient P are detected by the X-ray detector 12a or the X-ray detector 12b.

As illustrated in FIG. 1, the image processing apparatus 100 includes an Analog/Digital (A/D) conversion unit 21, the image memory 22, a subtraction unit 23, a filtering unit 24, a three-dimensional image processing unit 25, another A/D conversion unit 26, a Lookup Table (LUT) 27, an affine transformation unit 28, a three-dimensional reconstructing unit 29, the controlling unit 30, an analyzing unit 31, and a display unit 40. Further, although not illustrated, the image processing apparatus 100 includes, for example, an input unit such as a mouse, a keyboard, a trackball, and/or a pointing device configured to receive various types of operations performed on the X-ray diagnosis apparatus 1 from the operator.

The display unit 40 is configured to display various types of images processed by the image processing apparatus 100 and various types of information such as a Graphical User Interface (GUI). For example, the display unit 40 may be configured with a Cathode Ray Tube (CRT) monitor or a liquid crystal display monitor. The A/D conversion unit 21 is connected to the X-ray detector 12a and is configured to convert an analog signal input thereto from the X-ray detector 12a into a digital signal and to store the digital signal resulting from the conversion into the image memory 22 as an X-ray acquired image. The A/D conversion unit 26 is connected to the X-ray detector 12b and is configured to convert an analog signal input thereto from the X-ray detector 12b into a digital signal and to store the digital signal resulting from the conversion into the image memory 22 as an X-ray acquired image.

The image memory 22 is configured to store therein the X-ray acquired images (projection data). For example, the image memory 22 stores therein projection data acquired by the first imaging system and projection data acquired by the second imaging system. Further, the image memory 22 is also configured to therein reconstructed data (volume data) reconstructed by the three-dimensional reconstructing unit 29 (explained later) and a three-dimensional display image generated by the three-dimensional image processing unit 25. Further, the image memory 22 is also configured to store therein a difference image generated by the subtraction unit 23 (explained later).

The subtraction unit 23 is configured to generate the difference image such as a Digital Subtraction Angiography (DSA) image. For example, the subtraction unit 23 generates a difference image between an acquired image generated from X-ray signals acquired in the absence of a contrast agent by performing a rotation imaging process on a patient and an acquired image generated from X-ray signals acquired in the presence of the contrast agent by performing a rotation imaging process on the patient. More specifically, the subtraction unit 23 generates the DSA image by using the pieces of projection data of a mask image and a contrast image acquired from substantially mutually-the-same direction and stored in the image memory 22.

The filtering unit 24 is configured to perform a spatial or temporal filtering process or the like. The LUT 27 is configured to perform a gray-scale conversion process. The affine transformation unit 28 is configured to enlarge or reduce the size of images, to move images, to rotate images, and the like.

The three-dimensional reconstructing unit 29 is configured to reconstruct reconstructed data (hereinafter, "three-dimensional image data" or "volume data") from the projection data acquired through the rotation imaging process performed by the X-ray imaging mechanism 10. For example, as the projection data, the three-dimensional reconstructing unit 29 uses the post-subtraction difference image stored in the image memory 22 as a result of the difference calculating process performed between the mask image and the contrast image by the subtraction unit 23 and reconstructs the volume data from the post-subtraction difference images. Alternatively, as the projection data, the three-dimensional reconstructing unit 29 may use the mask image and the contrast image stored in the image memory 22 as a result of the conversion into the digital data performed by the A/D conversion unit 21 or the A/D conversion unit 26 and reconstruct the volume data from the projection data. After that, the three-dimensional reconstructing unit 29 stores the reconstructed volume data into the image memory 22.

In this situation, the three-dimensional reconstructing unit 29 according to the first embodiment reconstructs the volume data by using the difference image generated by the subtraction unit 23 on the basis of the mask image and the contrast image acquired by the first imaging system and the difference image generated by the subtraction unit 23 on the basis of the mask image and the contrast image acquired by the second imaging system. In other words, the three-dimensional reconstructing unit 29 reconstructs the volume data by using two-dimensional X-ray images acquired from two imaging systems. The generation of the volume data mentioned above will be explained later.

The three-dimensional image processing unit 25 is configured to generate a three-dimensional display image from the volume data stored in the image memory 22. For example, the three-dimensional image processing unit 25 generates a three-dimensional display image such as a volume rendering image, a surface rendering image, a maximum intensity projection (MIP) image, a minimum intensity projection image (MinIP) or a Multi Planar Reconstruction (MPR) image from the volume data. After that, the three-dimensional image processing unit 25 stores the generated three-dimensional display image into the image memory 22.

The controlling unit 30 is configured to control the entirety of the X-ray diagnosis apparatus 1. More specifically, the controlling unit 30 controls various types of processes related to the X-ray image taking process performed by the X-ray imaging mechanism 10, the image reconstructing process, a display image generating process, and a display image displaying process performed by the display unit 40. Further, the controlling unit 30 is configured to receive a setting of a region of interest from the operator.

The analyzing unit 31 is configured to generate blood flow information by analyzing the reconstructed three-dimensional blood vessel images in a time series. For example, as the blood flow information, the analyzing unit 31 derives a Cerebral Blood Volume (CBV) value, a Cerebral Blood Flow (CBF) value, a Mean Transit Time (MTT), and the like. In this situation, the CBV value indicates the amount of blood that is present in a tissue. The CBF value indicates the amount of blood flow flowing through a tissue per unit time period. The MTT indicates an average passing speed of the blood flowing through a tissue. The analyzing unit 31 may be configured so as to derive at least one selected from among the CBV value, the CBF value, the MTT, and the like.

In this situation, the image memory 22 may be configured by using, for example, a semiconductor memory device such as a Random Access Memory (RAM), a flash memory, or the like or a storage device such as a hard disk, an optical disk, or the like. Further, the subtraction unit 23, the filtering unit 24, the three-dimensional image processing unit 25, the LUT 27, the affine transformation unit 28, the three-dimensional reconstructing unit 29, the controlling unit 30, and the analyzing unit 31 may be configured by using, for example, an electronic circuit such as a Central Processing Unit (CPU), a Micro Processing Unit (MPU), or the like or an integrated circuit such as an Application Specific Integrated Circuit (ASIC), a Field Programmable Gate Array (FPGA), or the like.

The X-ray diagnosis apparatus 1 configured as described above can be used for, for example, angiographic diagnosis or interventional radiology such as the one described below. During a angiographic diagnosis or interventional radiology, a device such as a guide wire or a catheter is inserted into an inguinal region or the like of the patient. Further, the treatment (e.g., a embolization process or a blood vessel dilatation using a balloon or a stent) is carried out by bringing the inserted device to a diseased region. In this situation, if the patient complains of a headache during the treatment or when the treatment is completed, it is necessary to check to see whether a cerebral infarction occurred due to the treatment.

In a conventional situation, if the patient complains of a headache during the treatment, the treatment is discontinued, and the patient is taken to a CT room so that a CT scan can be performed. Also, in a conventional situation, when the treatment is completed, the patient is taken to a CT room after hemostasis, so that a CT scan can be performed. After that, if a sign of a cerebral infarction is recognized in a CT image or CT perfusion data as a result of the CT scan, a thrombolytic therapy is subsequently started.

In these conventional examples, however, it takes time to move the patient to the CT room after the hemostasis. For example, even in the situation where the patient complains of a headache during the treatment, and where a sign of a cerebral infarction needs to be checked urgently, it takes at least 30 minutes for transportation of a patient to CT room and preparation for CT scanning. When it is not urgent and it is checked to see whether a cerebral infarction occurred or not after the completion of the treatment, it may take at least three hours for those. Generally speaking, when a cerebral infarction has occurred, the quality of life (QOL) of the patient depends on how much time elapses before reperfusion is started. When the time period between a diagnosis of a cerebral infarction and the start of reperfusion is long, the patient may die in the worst case. For this reason, it is necessary to shorten, as much as possible, the time period that elapses before the start of the reperfusion. In other words, in the conventional diagnosis or treatment using an X-ray diagnosis apparatus, the patient is moved to a CT room so as to make a diagnosis of a cerebral infarction, and the patient is moved again from the CT room to another treatment room in order to further perform a thrombolytic therapy or a mechanical thrombectomy procedure. In addition, when the patient is moved from one room to another in this manner, it also takes time to prepare the rooms to accommodate the patient. If a cerebral infarction has occurred, it could be critical to take such time.

To cope with this situation, the X-ray diagnosis apparatus 1 according to the first embodiment makes it possible to make a diagnosis of a cerebral infarction, by configuring the X-ray diagnosis apparatus 1 itself to acquire data and to reconstruct three-dimensional blood vessel images in a time series, when a patient complains of a headache during a treatment or when it is checked to see whether a cerebral infarction has occurred or not at the time of the completion of a treatment.

In this situation, the X-ray diagnosis apparatus 1 is configured to reconstruct three-dimensional medical agent distribution images in a time series from a group of acquired images acquired in the presence of a medical agent by an imaging system from directions in a range that makes it possible to reconstruct three-dimensional images of the patient, by performing an iterative reconstruction process that uses at least one selected from between spatial continuity of the medical agent and temporal continuity of the concentration of the medical agent as a constraint condition.

In other words, as the three-dimensional medical agent distribution images in the time series, the X-ray diagnosis apparatus 1 reconstructs three-dimensional blood vessel images in a time series from the acquired images, i.e., from a group of acquired images generated from X-ray signals acquired in the absence of the contrast agent by the X-ray imaging mechanism 10 by performing a rotation imaging process on the patient and a group of acquired images generated from X-ray signals acquired in the presence of the contrast agent by the X-ray imaging mechanism 10 by performing a rotation imaging process on the patient, by performing the iterative reconstruction process that uses at least one selected from between spatial continuity of a blood vessel structure of which the image contrast is enhanced by the contrast agent and temporal continuity of the medical agent concentration as the constraint condition. For example, the X-ray diagnosis apparatus 1 generates a group of difference images from the group of acquired images generated from the X-ray signals acquired in the absence of the contrast agent by performing the rotation imaging process on the patient and the group of acquired images generated from the X-ray signals acquired in the presence of the contrast agent by performing the rotation imaging process on the patient. After that, the X-ray diagnosis apparatus 1 reconstructs the three-dimensional blood vessel images in the time series from the group of difference images, by performing the iterative reconstruction process that uses at least one selected from between the spatial continuity of the blood vessel structure and the temporal continuity of the medical agent concentration as the constraint condition.

Figure 2:
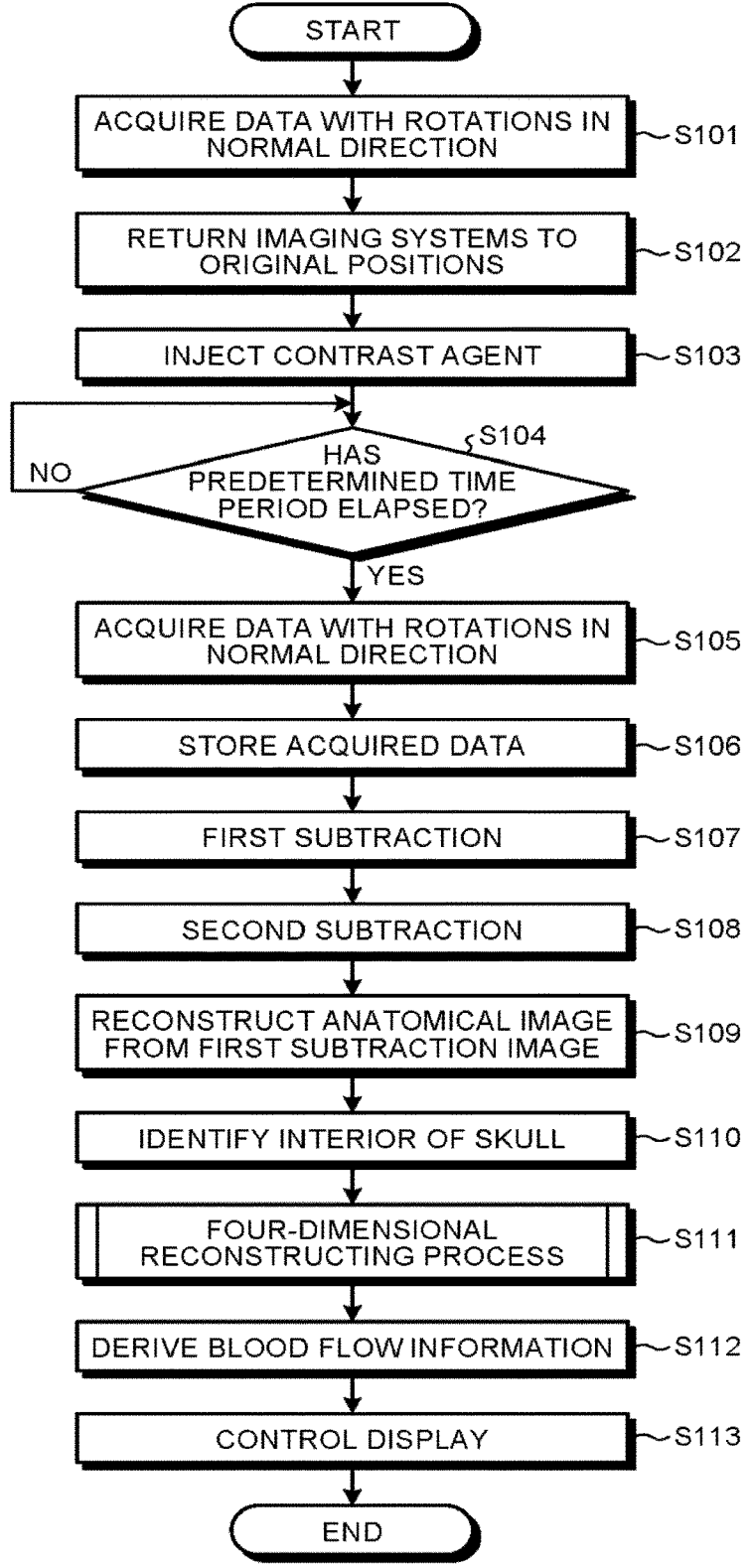
FIG. 2 is a flowchart of an exemplary procedure in a process performed by the X-ray diagnosis apparatus according to the first embodiment.

Next, an example of a process performed by the X-ray diagnosis apparatus 1 according to the first embodiment will be explained, with reference to FIG. 2. FIG. 2 is a flowchart of an exemplary procedure in the process performed by the X-ray diagnosis apparatus 1 according to the first embodiment. As illustrated in FIG. 2, in the X-ray diagnosis apparatus 1, the X-ray imaging mechanism 10 acquires mask images by using a bi-plane method under the control of the controlling unit 30 (step S101). For example, the X-ray diagnosis apparatus 1 acquires pieces of image data by rotating the first imaging system and the second imaging system in the normal direction before a contrast agent is injected. More specifically, the X-ray diagnosis apparatus 1 sets one of the imaging systems to the front of the patient and sets the other imaging system to a side of the patient. After that, starting from the state described above, the X-ray diagnosis apparatus 1 rotates the two imaging systems at an angular speed of 30 degrees/second at the same time in mutually the same direction, so that the imaging process at 90 degrees per three seconds is performed at the rate of 30 pps (pairs per second). In the description above, the example is explained in which the mask images are acquired by the first and the second imaging systems at the same time; however, another arrangement is also acceptable in which mask images are acquired by each of the imaging systems at a time.

Next, the timing with which the X-rays are emitted by the first imaging system and the second imaging system will be explained. FIG. 3 is a first drawing for explaining the first embodiment. The upper section of FIG. 3 illustrates the timing with which the X-rays are emitted by the first imaging system, whereas the lower section of FIG. 3 illustrates the timing with which the X-rays are emitted by the second imaging system. As illustrated in the upper section of FIG. 3, the first imaging system emits X-rays at time $T_1$, and subsequently, emits X-rays at time $T_3$, which is 33.3 milliseconds later. Further, subsequent to the X-ray emission at time $T_3$, the first imaging system emits X-rays at time $T_5$, which is 33.3 milliseconds later.

In contrast, as indicated in the lower section of FIG. 3, the second imaging system emits X-rays at time $T_2$, and subsequently, emits X-rays at time $T_4$, which is 33.3 milliseconds later. Further, subsequent to the X-ray emission at time $T_4$, the second imaging system emits X-rays at time $T_6$, which is 33.3 milliseconds later. In other words, the first imaging system and the second imaging system emit X-rays with alternate timing.

Returning to the description of FIG. 2, after having acquired the mask images, the X-ray diagnosis apparatus 1 returns the first imaging system and the second imaging system to the original positions by rotating the first and the second imaging systems in the opposite direction (step S102). When the first and the second imaging systems have returned to the original positions, the X-ray diagnosis apparatus 1 transmits a driving signal to the injector 50 so as to inject a contrast agent into the patient (step S103). For example, the injector 50 injects the contrast agent into the patient for one second at the rate of 2 to 3 cc/second. Subsequently, the X-ray diagnosis apparatus 1 judges whether or not a predetermined time period has elapsed (step S104). When having determined that the predetermined time period has not yet elapsed (step S104: No), the X-ray diagnosis apparatus 1 repeatedly performs the judging process until the predetermined time period elapses. The predetermined time period in this situation is a time period it takes for the contrast agent to reach a capillary phase. When a catheter is placed in a starting section of the internal carotid artery, the predetermined time period may be 2 to 3 seconds, for example.

When the X-ray diagnosis apparatus 1 has determined that the predetermined time period has elapsed (step S104: Yes), the X-ray imaging mechanism 10 acquires contrast images by using a bi-plane method, under the control of the controlling unit 30 (step S105). For example, after the contrast agent is injected, the X-ray diagnosis apparatus 1 rotates the first imaging system and the second imaging system in the normal direction so as to acquire pieces of image data, similarly to the imaging process at step S101. In this situation, for example, the X-ray diagnosis apparatus 1 rotates the two imaging systems at an angular speed of 30 degrees/second at the same time in mutually the same direction, so that the imaging process at 90 degrees per three seconds is performed at the rate of 30 pps (pairs per second). The group of contrast images acquired at step S105 in this manner represents images acquired while the contrast agent is reaching the capillary phase.

When the imaging process is completed, the X-ray diagnosis apparatus 1 at first stores the acquired image data into the image memory 22 (step S106). After that, the acquired image data is transferred to the subtraction unit 23. The subtraction unit 23 performs a subtraction between pre-contrast-enhancement images and calibration images (step S107). The calibration images are images taken while there is nothing but air between the X-ray tube 11a and the X-ray detector 12a or between the X-ray tube 11b and the X-ray detector 12b. The calibration images are taken during a calibration operation that is performed once in a number of months. The difference images generated by a first subtraction will be referred to as first subtraction images. The first subtraction images are transferred to the three-dimensional reconstructing unit 29. Subsequently, the subtraction unit 23 performs a subtraction between pre-contrast-enhancement images and post-contrast-enhancement images that were taken at substantially the same angle as each other (step S108). DSA images generated through this subtraction process called a second subtraction are similarly transferred to the three-dimensional reconstructing unit 29.

The three-dimensional reconstructing unit 29 reconstructs a three-dimensional image of the anatomical structure from the first subtraction images (step S109). As a result, the reconstructed three-dimensional image of the anatomical structure is displayed on the display unit 40. Further, the operator sets the interior of skull, for example, as a region of interest. Subsequently, the three-dimensional reconstructing unit 29 identifies the interior of the skull set as the region of interest, within the reconstructed three-dimensional image of the skull (step S110).

After that, the three-dimensional reconstructing unit 29 performs a four-dimensional reconstructing process to reconstruct three-dimensional blood vessel images in a time series from the DSA images (step S111). In this situation, the three-dimensional reconstructing unit 29 reconstructs a group of three-dimensional blood vessel images in a time series, for the interior of the skull. In other words, the three-dimensional reconstructing unit 29 reconstructs the three-dimensional blood vessel images in the time series from the group of difference images, by performing an iterative reconstruction process that uses the constraint condition, in the region of interest that was set. Details of the four-dimensional reconstructing process at step S111 will be explained later. Further, when the four-dimensional reconstructing process is finished, the reconstructed three-dimensional blood vessel images in the time series are transferred to the analyzing unit 31.

The analyzing unit 31 derives blood flow information such as a CBF value, a CBV value, a MTT, and the like by analyzing the reconstructed three-dimensional blood vessel images in the time series, in the same manner as in a CTP process (step S112). After that, the X-ray diagnosis apparatus 1 causes the derived blood flow information to be displayed (step S113).

Figure 4:
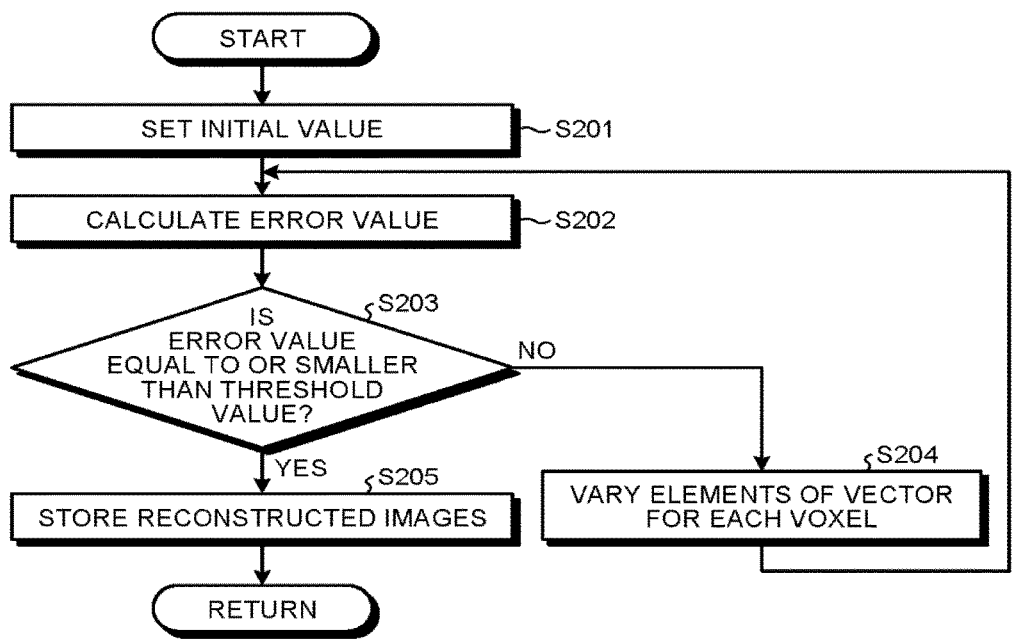
FIG. 4 is a flowchart of a procedure in a reconstructing process performed by a three-dimensional reconstructing unit according to the first embodiment.

Next, a procedure in the four-dimensional reconstructing process performed by the three-dimensional reconstructing unit 29 will be explained, with reference to FIG. 4. FIG. 4 is a flowchart of the procedure in the reconstructing process performed by the three-dimensional reconstructing unit 29 according to the first embodiment. The processing procedure indicated in FIG. 4 corresponds to the process at step S111 in FIG. 2. As the three-dimensional medical agent distribution images in the time series, the three-dimensional reconstructing unit 29 reconstructs the three-dimensional blood vessel images in the time series from the group of acquired images generated from the X-ray signals acquired in the absence of the contrast agent by the imaging system by performing the rotation imaging process on the patient and the group of acquired images generated from the X-ray signals acquired in the presence of the contrast agent by the imaging system by performing the rotation imaging process on the patient, by performing the iterative reconstruction process that uses at least one selected from between the spatial continuity of the blood vessel structure of which the image contrast is enhanced by the contrast agent and the temporal continuity of the medical agent concentration as the constraint condition.

As illustrated in FIG. 4, the three-dimensional reconstructing unit 29 sets an initial value (step S201). Subsequently, the three-dimensional reconstructing unit 29 calculates an error (which may be called an "error value") (step S202). In this situation, the three-dimensional reconstructing unit 29 performs the four-dimensional reconstructing process by solving Expression (1) presented below.

$$E = \|\vec{g} - H\vec{f}\|^2 + \alpha \|\vec{f}\|_{TV}^2 \qquad (1)$$

In Expression (1), the f-vector is obtained by arranging elements (voxel values) of the reconstructed image in a row. Further, the g-vector is obtained by arranging elements (pixel values) of the acquired DSA image in a row. Further, a Total Variation (TV) of the f-vector indicates the constraint condition. H denotes a projection matrix identifying an involvement of the f-vector in the g-vector. Further, $\alpha$ is a factor used for adjusting contributions of the term of TV and the projection image to the error value and is determined empirically. Further, the TV of the f-vector can be expressed as indicated in Expression (2) below.

$$\|\vec{f}\|_{TV} = \sum_{i,j,k,l} |\vec{\nabla} f_{i,j,k,l}| = \sum_{i,j,k,l} \sqrt{\begin{array}{c}(f_{i,j,k,l} - f_{i-1,j,k,l})^2 + (f_{i,j,k,l} - f_{i,j-1,k,l})^2 + \\ (f_{i,j,k,l} - f_{i,j,k-1,l})^2 + (f_{i,j,k,l} - f_{i,j,k,l-1})^2\end{array}} \qquad (2)$$

Figure 5A:
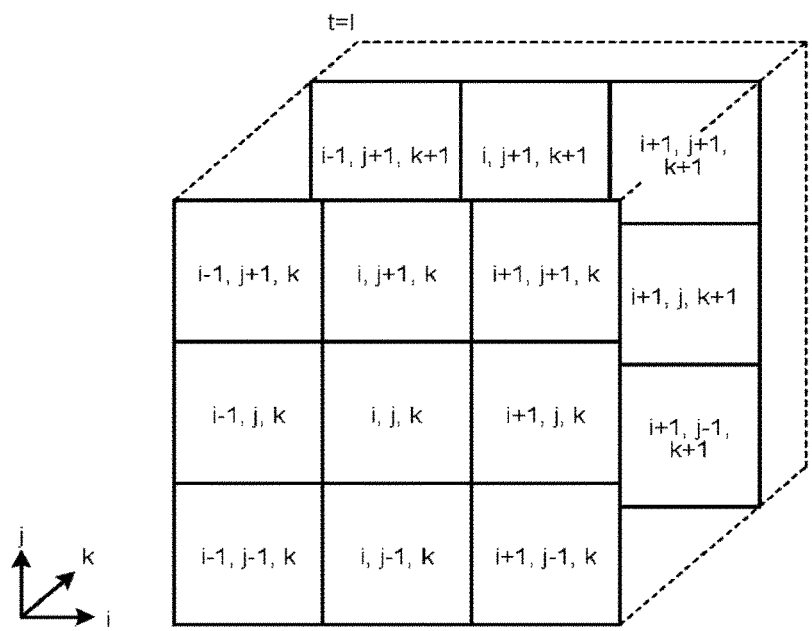
FIG. 5A is a second drawing for explaining the first embodiment.
Figure 5B:
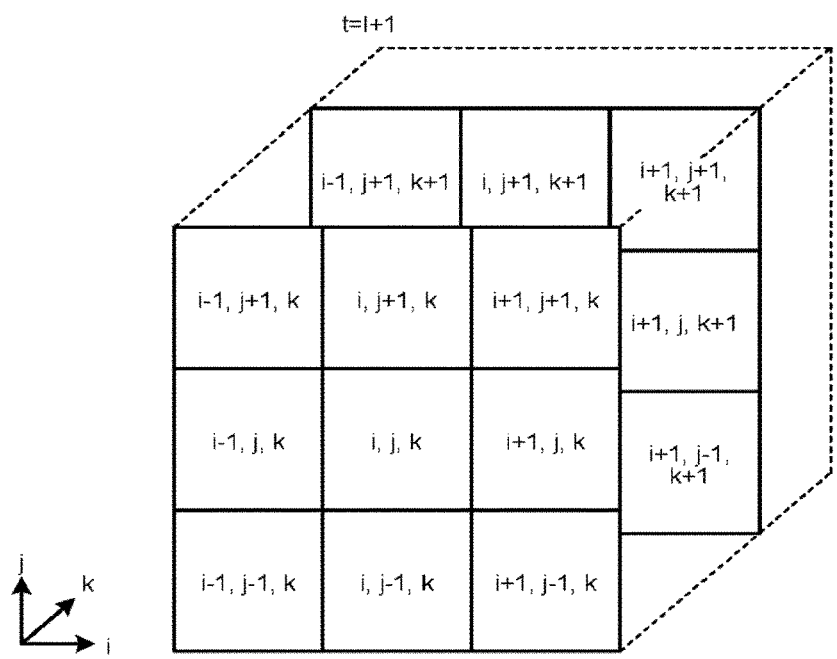
FIG. 5B is a third drawing for explaining the first embodiment.

In Expression (2), (i,j,k) denotes the spatial coordinates of the reconstruction space, whereas l denotes a time or the number of imaged frames. The constraint condition in Expression (2) will be explained, with reference to FIGS. 5A and 5B. FIG. 5A is a second drawing for explaining the first embodiment. FIG. 5B is a third drawing for explaining the first embodiment.

FIG. 5A indicates the coordinates of a three-dimensional image when time t is equal to l. FIG. 5B indicates the coordinates of the three-dimensional image when time t is equal to l+1. Further, in FIGS. 5A and 5B, a three-dimensional orthogonal coordinate system having i-, j-, and k-axes is defined. For the sake of convenience in the explanation, FIGS. 5A and 5B each illustrate only the three sets of coordinates on the i-axis, the three sets of coordinates on the j-axis, and the two sets of coordinates on the k-axis, from among the coordinates of the three-dimensional image.

As indicated in Expression (2), for each of the sets of coordinates, the three-dimensional reconstructing unit 29 defines the difference in only one direction on each of the i-, j-, and k-axes as the constraint condition. For example, with respect to the coordinates (i+1, j+1, k+1) corresponding to t=l+1 indicated in FIG. 5B, the coordinates (i, j+1, k+1) corresponding to t=l+1, the coordinates (i+1, j, k+1) corresponding to t=l+1, and the coordinates (i+1, j+1,k) corresponding to t=l+1 indicated in FIG. 5B are used as a spatial constraint condition. Further, for example, with respect to the coordinates (i+1, j+1, k+1) corresponding to t=l+1 indicated in FIG. 5B, the coordinates (i+1, j+1, k+1) corresponding to t=l indicated in FIG. 5A are used as a temporal constraint condition. In this situation, the spatial constraint condition is based on the notion that no rapid change occurs because the capillaries are continuous. The temporal constraint condition is based on the notion that the blood flows i. In other words, the spatial constraint condition is based on the notion that the blood vessel structure in which the contrast agent administered to the patient P is distributed does not rapidly change morphologically. The temporal constraint condition is based on the notion that the concentration of the contrast agent administered to the patient P does not fluctuate quickly at mutually the same coordinates of the three-dimensional images. In other words, the X-ray diagnosis apparatus 1 uses, for example, the blood vessel structure in which the contrast agent administered to the patient P is distributed as the constraint condition based on the spatial continuity of the medical agent. Further, the X-ray diagnosis apparatus 1 uses the concentration of the contrast agent at mutually the coordinates in the three-dimensional image as the constraint condition based on the temporal continuity of the concentration of the medical agent.

Returning to the description of FIG. 4, the three-dimensional reconstructing unit 29 judges whether the error value calculated at step S202 is equal to or smaller than a threshold value (step S203). In this situation, if the error value is not determined to be equal to or smaller than the threshold value (step S203: No), the three-dimensional reconstructing unit 29 varies the elements of the vector for each of the voxels (step S204), and the process proceeds to step S202.

On the contrary, when the error value is determined to be equal to or smaller than the threshold value (step S203: Yes), the three-dimensional reconstructing unit 29 stores the reconstructed image in the image memory 22 (step S205), and the process is ended. As explained herein, as an optimizing procedure, the three-dimensional reconstructing unit 29 finely varies the elements of the f-vector for each of the voxels and judges whether the error value becomes smaller due to the varying. After that, when the error value calculated by using Expression (1) eventually becomes sufficiently small, the three-dimensional reconstructing unit 29 ends the reconstructing process. In other words, during the iterative reconstruction process, the three-dimensional reconstructing unit 29 calculates the error value by adding the constraint condition to the difference between the pixel value obtained by projecting an estimated voxel value of the three-dimensional image onto each of the plurality of X-ray signal detection planes and the pixel value of each of the difference images and repeatedly performs the reconstructing process until the error value becomes smaller than the predetermined threshold value. In this situation, the three-dimensional reconstructing unit 29 calculates the error value by adding the constraint condition to the difference between the pixel value obtained by projecting an estimated voxel value of the three-dimensional image onto each of the plurality of X-ray signal detection planes and the pixel value of each of the difference images corresponding to the projection directions toward the detection planes.

As explained above, the X-ray diagnosis apparatus 1 according to the first embodiment reconstructs the three-dimensional blood vessel images in the time series as a result of the data acquisition process performed by the X-ray diagnosis apparatus 1 itself, for example, when the patient complains of a headache during a treatment or when it is checked to see whether a cerebral infarction has occurred or not at the time of the completion of a treatment. With this arrangement, the X-ray diagnosis apparatus 1 according to the first embodiment makes it possible to make a diagnosis of a cerebral infarction without having to move the patient to a CT room. As a result, the X-ray diagnosis apparatus 1 according to the first embodiment is able to shorten the time period it takes before a treatment is started when a cerebral infarction has occurred.

Further, because the X-ray diagnosis apparatus 1 according to the first embodiment performs the iterative reconstruction process while using the constraint condition, it is possible to select an appropriate solution from among innumerable solutions. As a result, the X-ray diagnosis apparatus 1 according to the first embodiment is able to accurately reconstruct the three-dimensional images in the time series.

Further, in the first embodiment described above, the example is explained in which the X-ray diagnosis apparatus is configured so that the X-rays are emitted by the first imaging system and the second imaging system with the mutually-different timing. However, possible embodiments are not limited to this example. For instance, the X-ray diagnosis apparatus may be configured so that the X-rays are emitted by the first imaging system and the second imaging system with mutually the same timing. FIG. 6 is a drawing for explaining a modification example of the first embodiment.

The upper section of FIG. 6 illustrates timing with which X-rays are emitted by the first imaging system, whereas the lower section of FIG. 6 illustrates timing with which X-rays are emitted by the second imaging system. As illustrated in the upper section of FIG. 6, the first imaging system emits X-rays at time $T_1$, and subsequently, emits X-rays at time $T_3$, which is 33.3 milliseconds later. Further, subsequent to the X-ray emission at time $T_3$, the first imaging system emits X-rays at time $T_5$, which is 33.3 milliseconds later.

Further, as indicated in the lower section of FIG. 6, the second imaging system emits X-rays at time $T_1$, and subsequently, emits X-rays at time $T_3$, which is 33.3 milliseconds later. Further, subsequent to the X-ray emission at time $T_3$, the second imaging system emits X-rays at time $T_5$, which is 33.3 milliseconds later. In other words, the first imaging system and the second imaging system emit X-rays with mutually the same timing. In that situation, a scattered ray component of the X-rays emitted by the first imaging system may be detected by the second imaging system, whereas a scattered ray component of the X-rays emitted by the second imaging system may be detected by the first imaging system. The contrast of the three-dimensional image of the anatomical structure reconstructed from the first subtraction is degraded by the scattered ray component. However, the interior of the skull is identified from the three-dimensional image of the anatomical structure on the basis of the skull. Because the skull is a bony structure, and the image thereof has high contrast to begin with, almost no impact is made thereon by the degradation of the contrast caused by the scattered rays. On the other hand, in the three-dimensional blood vessel images in the time series reconstructed from the second subtraction, because the scattered ray component contained in the mask images substantially match the scattered ray component contained in the contrast images, the scattered ray component is cancelled out. For this reason, the impact of the scattered rays on the three-dimensional blood vessel images in the time series is substantially negligible.

Further, in the first embodiment above, the example of the X-ray diagnosis apparatus including the bi-plane mechanism is explained; however, possible embodiments are not limited to this example. For instance, the X-ray imaging mechanism 10 included in the X-ray diagnosis apparatus may be a single-plane imaging mechanism including a single imaging system.

Second Embodiment

In the first embodiment, the example is explained in which the radiation diagnosis apparatus is the X-ray diagnosis apparatus 1; however, the radiation diagnosis apparatus is not limited to an X-ray diagnosis apparatus and may be, for example, an X-ray Computed Tomography (CT)

apparatus. Thus, in a second embodiment, an X-ray CT apparatus will be explained, as an example of the radiation diagnosis apparatus.

Figure 7:
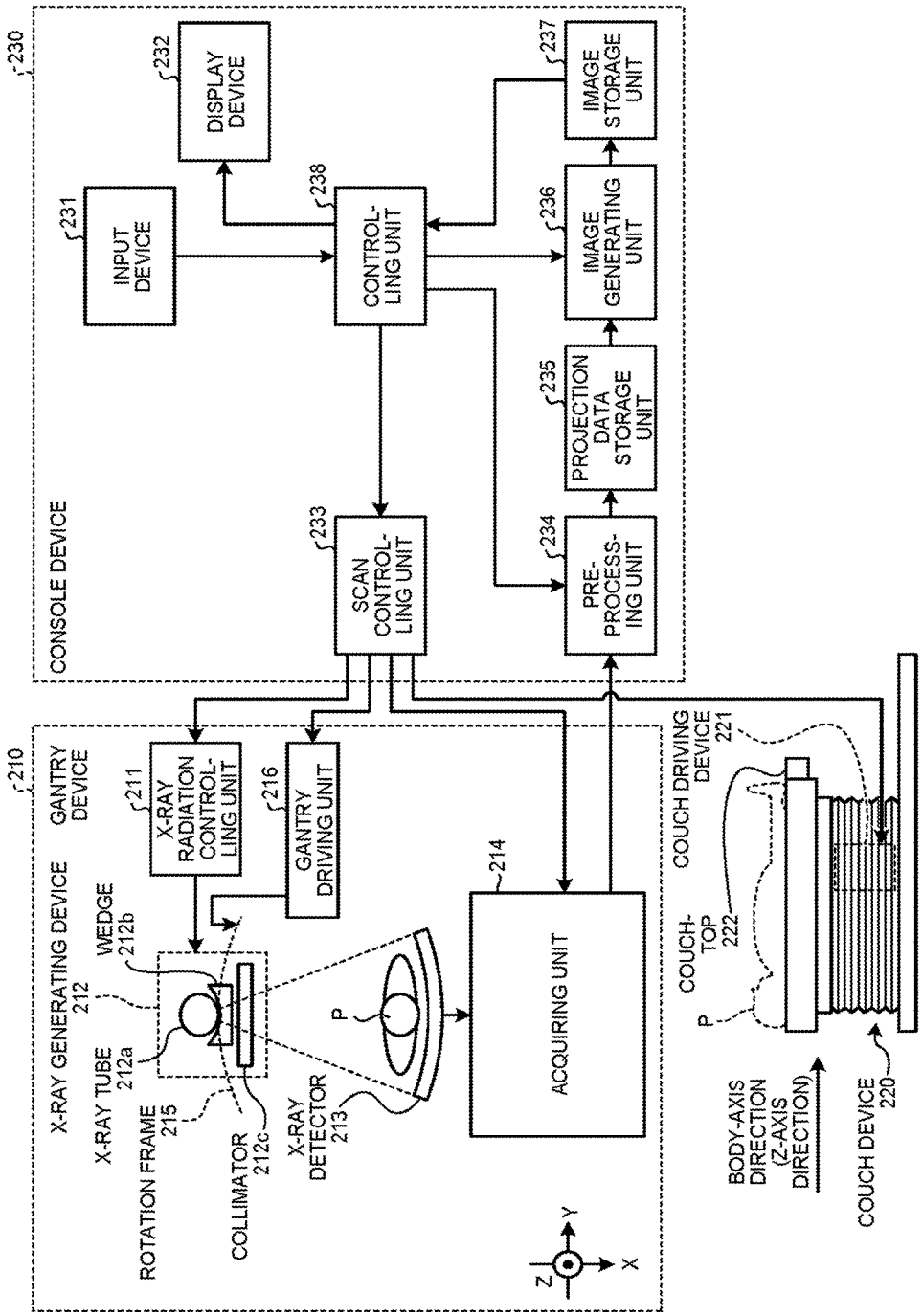
FIG. 7 is a block diagram of an exemplary configuration of an X-ray CT apparatus according to a second embodiment.

First, a configuration of an X-ray CT apparatus according to the second embodiment will be explained. FIG. 7 is a block diagram of an exemplary configuration of the X-ray CT apparatus according to the second embodiment. As illustrated in FIG. 7, the X-ray CT apparatus according to the second embodiment includes a gantry device 210, a couch device 220, and a console device 230.

The gantry device 210 is a device configured to radiate X-rays onto the patient P and to acquire projection data from detection data of X-rays that have passed through the patient P. The gantry device 210 includes an X-ray radiation controlling unit 211, an X-ray generating device 212, an X-ray detector 213, an acquiring unit 214, a rotation frame 215, and a gantry driving unit 216.

The rotation frame 215 is configured to support the X-ray generating device 212 including an X-ray tube 212a (explained later) and the X-ray detector 213, so as to be rotatable around the patient P. The rotation frame 215 is an annular-shaped frame configured to support the X-ray generating device 212 and the X-ray detector 213 so as to oppose each other while the patient P is interposed therebetween and to be driven by a gantry driving unit 216 (explained later) to rotate at a high-speed on a circular orbit centered on the patient P.

The X-ray generating device 212 is a device configured to generate X-rays and to radiate the generated X-rays onto the patient P. The X-ray generating device 212 includes the X-ray tube 212a, a wedge 212b, and a collimator 212c.

The X-ray tube 212a is configured to emit the X-rays. More specifically, the X-ray tube 212a is a vacuum tube configured to generate an X-ray beam onto the patient P by using a high voltage supplied thereto by the X-ray radiation controlling unit 211 (explained later). The X-ray tube 212a is configured to emit the X-ray beam onto the patient P, in conjunction with the rotations of the rotation frame 215. The X-ray tube 212a is configured to generate the X-ray beam that spreads at a fan angle and a cone angle.

The wedge 212b is an X-ray filter used for adjusting the X-ray dose of the X-rays emitted from the X-ray tube 212a. The collimator 212c is a slit used for narrowing the radiation range of the X-rays of which the X-ray dose was adjusted by the wedge 212b, under control of the X-ray radiation controlling unit 211 (explained later).

The X-ray radiation controlling unit 211 is a device that serves as a high-voltage generating unit and is configured to supply the high voltage to the X-ray tube 212a. The X-ray tube 212a is configured to generate the X-rays by using the high voltage supplied thereto from the X-ray radiation controlling unit 211. By adjusting the X-ray tube voltage and the X-ray tube current supplied to the X-ray tube 212a, the X-ray radiation controlling unit 211 is configured to adjust the X-ray dose to be radiated onto the patient P. Further, the X-ray radiation controlling unit 211 is configured to adjust the radiation range (the fan angle or the cone angle) of the X-rays, by adjusting the degree of aperture of the collimator 212c.

Under the control of the X-ray radiation controlling unit 211, the X-ray tube 212a is capable of continuously emitting X-rays in the entire surrounding of the patient P so as to realize a full reconstructing process and of continuously emitting X-rays in an emission range (180 degrees+the fan angle) that makes it possible to perform a half reconstructing process so as to realize the half reconstructing process.

The gantry driving unit 216 is configured to cause the X-ray generating device 212 and the X-ray detector 213 to turn on the circular orbit centered on the patient P, by driving the rotation frame 215 to rotate.

The X-ray detector 213 is configured to detect the X-rays that were emitted from the X-ray tube 212a and have passed through the patient P. More specifically, the X-ray detector 213 detects the X-rays that were emitted from the X-ray tube 212a and have passed through the patient P, by employing X-ray detecting elements that are arranged two-dimensionally.

The acquiring unit 214 is a data acquisition system (DAS) configured to acquire projection data from detection data of the X-rays detected by the X-ray detector 213. For example, the acquiring unit 214 generates the projection data by performing an amplifying process, an A/D conversion process, an inter-channel sensitivity correcting process, and/or the like on X-ray intensity distribution data detected by the X-ray detector 213 and transmits the generated projection data to the console device 230 (explained later). For example, when X-rays are continuously emitted from the X-ray tube 212a while the rotation frame is rotating, the acquiring unit 214 acquires a group of projection data corresponding to the entire surrounding (corresponding to 360 degrees). Further, the acquiring unit 214 brings the acquired pieces of projection data into correspondence with X-ray tube positions and transmits the result to the console device 230 (explained later). The X-ray tube positions serve as information indicating the projection directions of the pieces of projection data. The inter-channel sensitivity correcting process may be performed by a pre-processing unit 234 (explained later).

The couch device 220 is a device on which the patient P is placed and includes a couchtop 222 and a couch driving device 221. The couchtop 222 is a board on which the patient P is placed. Under control of a scan controlling unit 233 (explained later), the couch driving device 221 moves the patient P to the inside of the rotation frame 215 (inside the image taking space) by moving the couchtop 222 in the Z-axis direction.

For example, the gantry device 210 performs a helical scan by which the patient P is helically scanned by rotating the rotation frame 215 while the couchtop 222 is being moved. Alternatively, the gantry device 210 may perform a conventional scan by which the patient P is scanned on a circular orbit by rotating the rotation frame 215, while the position of the patient P is fixed after the couchtop 222 is moved. Alternatively, the gantry device 210 may implement a step-and-shoot method by which the conventional scan is performed in a plurality of scan areas, by moving the position of the couchtop 222 at regular intervals.

The console device 230 is a device configured to receive operations performed on the X-ray CT apparatus by an operator and to reconstruct X-ray CT image data from the X-ray detection data acquired by the gantry device 210. The console device 230 includes an input device 231, a display device 232, the scan controlling unit 233, the pre-processing unit 234, a projection data storage unit 235, an image generating unit 236, an image storage unit 237, and a controlling unit 238.

The input device 231 includes a mouse, a keyboard, a button, a pedal (a foot switch), and/or the like used by the operator of the X-ray CT apparatus to input various types of instructions and various types of settings and is configured to transfer information about the instructions and the settings received from the operator, to the controlling unit 238.

The display device 232 is a monitor referenced by the operator and is configured, under the control of the controlling unit 238, to display the X-ray CT image data for the operator and to display a Graphical User Interface (GUI) used for receiving the various types of instructions and the various types of settings from the operator via the input device 231. For example, by using the input device 231, the operator inputs examination information such as a posture, during an image taking process, of the patient P placed on the couchtop 222, to a GUI for an examination-information registration purpose.

Under the control of the controlling unit 238 (explained later), the scan controlling unit 233 is configured to control the projection data acquiring process performed by the gantry device 210, by controlling operations of the X-ray radiation controlling unit 211, the gantry driving unit 216, the acquiring unit 214, and the couch driving device 221.

The pre-processing unit 234 is configured to generate post-correction projection data by performing a logarithmic conversion process and correcting processes such as an offset correction, a sensitivity correction, a beam hardening correction, and the like on the projection data generated by the acquiring unit 214. In the following sections, the post-correction projection data generated by the pre-processing unit 234 will be referred to as reconstruction-purpose projection data.

The projection data storage unit 235 is configured to store therein the reconstruction-purpose projection data generated by the pre-processing unit 234. Further, the projection data storage unit 235 is also configured to store therein the projection data acquired by the acquiring unit 214. In this situation, the projection data storage unit 235 stores therein the X-ray tube positions so as to be kept in correspondence with the projection data generated by the pre-processing unit 234 and the projection data generated by the acquiring unit 214. The image storage unit 237 is configured to store therein various types of image data generated by the image generating unit 236.

The image generating unit 236 is a processing unit configured to generate the various types of image data by using the projection data stored in the projection data storage unit 235. For example, the image generating unit 236 is configured to generate a difference image between an acquired image generated from X-ray signals acquired in the absence of a contrast agent by performing a rotation imaging process on a patient and an acquired image generated from X-ray signals acquired in the presence of the contrast agent by performing a rotation imaging process on the patient. Further, for example, the image generating unit 236 is configured to reconstruct three-dimensional blood vessel images in a time series from difference images.

Further, the image generating unit 236 is configured to generate blood flow information by analyzing the reconstructed three-dimensional blood vessel images in the time series. For example, as the blood flow information, the image generating unit 236 derives a Cerebral Blood Volume (CBV) value, a Cerebral Blood Flow (CBF) value, a Mean Transit Time (MTT), and the like.

The controlling unit 238 exercises overall control of the X-ray CT apparatus by controlling operations of the gantry device 210, the couch device 220, and the console device 230. More specifically, the controlling unit 238 controls the scans performed by the gantry device 210 by controlling the scan controlling unit 233. Further, the controlling unit 238 controls the image reconstructing process and the image generating process performed by the console device 230, by controlling the pre-processing unit 234 and the image generating unit 236. Furthermore, the controlling unit 238 exercises control so that any of the various types of image data stored in the image storage unit 237 is displayed by the display device 232. In addition, the controlling unit 238 receives a setting of a region of interest from the operator.

In this situation, the projection data storage unit 235 and the image storage unit 237 may be configured by using, for example, a semiconductor memory device such as a Random Access Memory (RAM), a flash memory, or the like or a storage device such as a hard disk, an optical disk, or the like. Further, the scan controlling unit 233, the pre-processing unit 234, the image generating unit 236, and the controlling unit 238 may be configured by using, for example, an electronic circuit such as a Central Processing Unit (CPU), a Micro Processing Unit (MPU), or the like or an integrated circuit such as an Application Specific Integrated Circuit (ASIC), a Field Programmable Gate Array (FPGA), or the like.

The X-ray CT apparatus according to the second embodiment configured as described above performs, for example, a CTP process to examine whether a cerebral infarction has occurred. For example, during a CTP process that uses the X-ray CT apparatus according to the second embodiment, a contrast agent is administered before acquiring mask images. Further, the mask images are acquired before the contrast agent reaches the neck region. Subsequently, after the contrast agent reaches the inside of the skull, contrast images are acquired. Alternatively, during a CTP process that uses the X-ray CT apparatus according to the second embodiment, a contrast agent may be injected after mask images are acquired, so as to acquire contrast images.

Subsequently, the image generating unit 236 reconstructs three-dimensional blood vessel images in a time series from the acquired images, i.e., an acquired image generated from the X-ray signals acquired in the absence of a contrast agent by performing a rotation imaging process on the patient and an acquired image generated from the X-ray signals acquired in the presence of the contrast agent by performing a rotation imaging process on the patient, by performing an iterative reconstruction process that uses at least one selected from between spatial continuity of a blood vessel structure and temporal continuity of a medical agent concentration, as a constraint condition.

For example, the image generating unit 236 generates a DSA image that is a difference image between the acquired image generated from the X-ray signals acquired in the absence of the contrast by performing the rotation imaging process on the patient agent and the acquired image generated from the X-ray signals acquired in the presence of the contrast agent by performing the rotation imaging process on the patient.

Subsequently, the image generating unit 236 reconstructs a three-dimensional image of the intracranial region from the DSA image. After that, the image generating unit 236 reconstructs three-dimensional blood vessel images in a time series from difference images by performing an iterative reconstruction process that uses at least one selected from between spatial continuity of the blood vessel structure and temporal continuity of the medical agent concentration, as a constraint condition. In this situation, the image generating unit 236 reconstructs the three-dimensional blood vessel images in the time series for the inside of the skull. Similarly to the process at step S111 in FIG. 2 (i.e., the processing procedure illustrated in FIG. 4), the image generating unit 236 performs the iterative reconstruction process by solving Expression (1) presented above. In that situation also, the TV of the f-vector can be expressed as indicated in Expression (2) presented above.

After that, when the iterative reconstruction process is finished, the image generating unit 236 analyzes the reconstructed three-dimensional blood vessel image data in the time series and derives blood flow information such as a CBF value, a CBV value, a MTT, and the like. Subsequently, the controlling unit 238 causes the derived blood flow information to be displayed.

As explained above, the X-ray CT apparatus according to the second embodiment performs the iterative reconstruction process by using the constraint condition. Accordingly, it is possible to select an appropriate solution from among innumerable solutions. As a result, the X-ray CT apparatus according to the second embodiment is able to accurately reconstruct the three-dimensional images in the time series.

Figure 8:
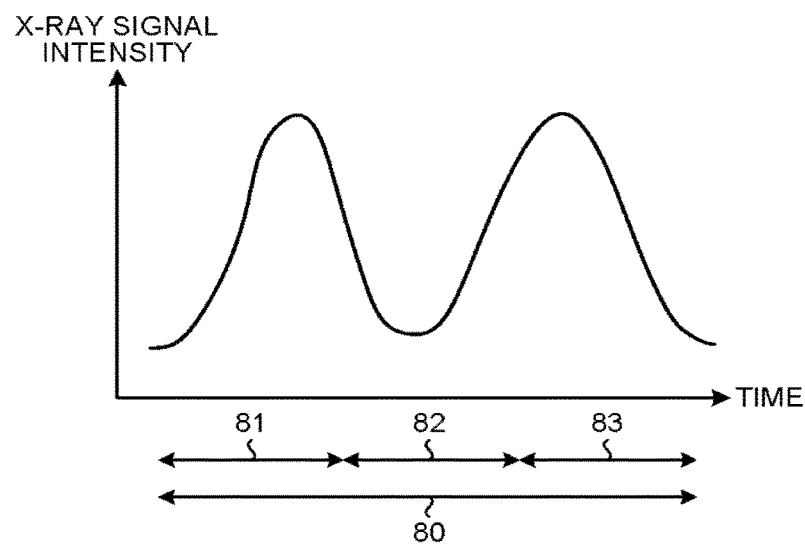
FIG. 8 is a drawing for explaining a reconstructing process performed by the X-ray CT apparatus according to the second embodiment.

Further, for example, when a scan time period at one time is 0.3 seconds, a conventional X-ray CT apparatus reconstructs a CT image every 0.3 seconds by using projection data acquired in the time period of 0.3 seconds. For this reason, the X-ray CT apparatus according to the second embodiment reconstructs three-dimensional blood vessel images in a time series from difference images generated at predetermined time intervals that are among the difference images sequentially generated during the time period of the rotation imaging process. FIG. 8 is a drawing for explaining a reconstructing process performed by the X-ray CT apparatus according to the second embodiment.

In FIG. 8, the horizontal axis expresses time, whereas the vertical axis expresses intensity of X-ray signals. A bidirectional arrow 80 in FIG. 8 indicates a scan time period corresponding to one rotation. In this situation, the scan time period for one rotation is set to 0.3 seconds. For example, when a scan time period for one rotation is 0.3 seconds, the X-ray CT apparatus according to the second embodiment reconstructs a CT image every 0.1 seconds by using projection data acquired in the time period of 0.1 seconds. More specifically, the X-ray CT apparatus according to the second embodiment reconstructs a group of three-dimensional blood vessel images in the time series from a group of difference images generated at the time intervals indicated by a bidirectional arrow 81, a bidirectional arrow 82, and a bidirectional arrow 83 in FIG. 8. In other words, the X-ray CT apparatus according to the second embodiment reconstructs the images by using the pieces of projection data acquired from every 120-degree rotation. It should be noted that the intensity of the X-ray signals is varied during each rotation for the purpose of preventing the intensity of the X-rays passing through the human body from varying depending on directions. For example, when a medical examination is performed on the head, because the frontal direction is often longer than the lateral direction, the amount of X-ray absorption is larger in the frontal direction. For this reason, it is a common practice to relatively raise the X-ray signal intensity for the frontal direction and to relatively lower the X-ray signal intensity for the lateral direction.

In this situation, a difference image generated on the basis of a contrast image acquired at the time interval indicated by the bidirectional arrow 81 in FIG. 8 will be referred to as a difference image $g_1$. A difference image generated on the basis of a contrast image acquired at the time interval indicated by the bidirectional arrow 82 will be referred to as a difference image $g_2$. A difference image generated on the basis of a contrast image acquired at the time interval indicated by the bidirectional arrow 83 will be referred to as a difference image $g_3$. The X-ray CT apparatus according to the second embodiment reconstructs $f_1$ from $g_1$, $f_2$ from $g_2$, and $f_3$ from $g_3$.

As explained above, the X-ray CT apparatus according to the second embodiment reconstructs the three-dimensional blood vessel images in the time series from the difference images generated at the predetermined time intervals that are among the difference images sequentially generated during the time period of the rotation imaging process. As a result, the X-ray CT apparatus according to the second embodiment is able to accurately reconstruct the images with a small data amount. Further, with these arrangements, the X-ray CT apparatus according to the second embodiment is able to reconstruct the images having a higher time resolutions than, for example, in the situation where a CT image is reconstructed every 0.3 seconds by using the projection data acquired in the time period of 0.3 seconds.

With reference to FIG. 8, the example is explained in which the scan time period indicated with the bidirectional arrow 80 is divided into the time periods that are indicated with the bidirectional arrows 81, 82, and 83 and do not overlap each other, so that the group of three-dimensional blood vessel images in the time series is reconstructed from the group of difference images generated in the corresponding time periods. However, possible embodiments are not limited to this example. For instance, it is acceptable to divide the time period of a rotation imaging process into time period sections that partially overlap with one another. More specifically, the time period of the rotation imaging process may be divided into time period sections in such a manner that the time periods indicated by the bidirectional arrows 81 and 82 in FIG. 8 partially overlap each other and that the time periods indicated by the bidirectional arrows 82 and 83 partially overlap each other.

In the second embodiment, the example is explained in which the three-dimensional blood vessel images in the time series are reconstructed from the difference images between the acquired images generated from the X-ray signals acquired in the absence of the contrast agent by performing the rotation imaging process on the patient and the acquired images generated from the X-ray signals acquired in the presence of the contrast agent by performing the rotation imaging process on the patient; however, possible embodiments are not limited to this example. For instance, another arrangement is acceptable in which a head CT image is reconstructed from an acquired image generated from X-ray signals acquired in the absence of a contrast agent by performing a rotation imaging process on a patient by using an existing reconstruction algorithm, and subsequently, an acquired image generated from X-ray signals acquired in the presence of the contrast agent by performing a rotation imaging process on the patient is reconstructed as a time change component with respect to the head CT image. More specifically, an f-vector is expressed as a sum of the head CT image and a temporal concentration change component of the contrast agent, so that the temporal concentration change component of the contrast agent can be calculated. The images reconstructed in this manner substantially match the three-dimensional blood vessel images in the time series reconstructed from the difference images.

In the second embodiment, the X-ray CT apparatus including the one pair made up of the X-ray tube and the X-ray detector is explained; however, possible embodiments are not limited to this example. For instance, the X-ray CT apparatus may be of a dual-source type, which includes two pairs each made up of an X-ray tube and an X-ray detector.

Other Embodiments

Possible embodiments are not limited to the embodiments described above.

For example, it is acceptable to also configure the X-ray diagnosis apparatus 1 according to the first embodiment in such a manner that, similarly to the X-ray CT apparatus in the second embodiment, three-dimensional blood vessel images in a time series are reconstructed from difference images generated at predetermined time intervals that are among the difference images sequentially generated during the time period of the rotation imaging process. As an example, a situation will be explained in which mask images and contrast images are acquired with rotations at an angular speed of 30 degrees/second so that the imaging process at 90 degrees per three seconds is performed at the rate of 30 pps (pairs per second). In that situation, the three-dimensional reconstructing unit 29 may generate the difference images with the mask images by using the contrast images acquired every second, so that three-dimensional blood vessel images in a time series are reconstructed by using the generated difference images.

Further, in the embodiments described above, the example is explained in which, during the four-dimensional reconstructing process, the elements of the f-vector are finely varied for each of the voxels, so that the reconstructing process is repeatedly performed until the error value becomes smaller than the predetermined threshold value due to the varying. In this situation, it is also acceptable to limit the region of the f-vector that is varied for each of the voxels. For example, when three-dimensional blood vessel images in which capillaries are emphasized are to be reconstructed, another arrangement is acceptable in which the elements of the f-vector only in the voxels corresponding to the capillary phase are varied, without varying the elements of the f-vector in the voxels corresponding to an artery phase and a vein phase.

Further, in Expression (2) above, the difference from only the one direction is defined as the constraint condition; however, possible embodiments are not limited to this example. For instance, spatially, the difference from four neighbors, six neighbors, eight neighbors, or 26 neighbors may be defined as a constraint condition. Further, temporally, the constraint condition may be defined on the basis of the differences from the frames before and after the frame or may be defined on the basis of the differences from the two frames before and after the frame. In the present example, the spatial continuity and the temporal continuity are collectively defined in one constraint condition as the TV. However, it is also acceptable to define the spatial continuity and the temporal continuity separately as constraint conditions. In this case, it is preferred to set different weighting factors for the spatial continuity and the temporal continuity to adjust contribution of two constraint conditions to fit clinical conditions. Further, as long as a similar effect is achieved, it is acceptable to use any other definition for the constraint condition.

Figure 9:
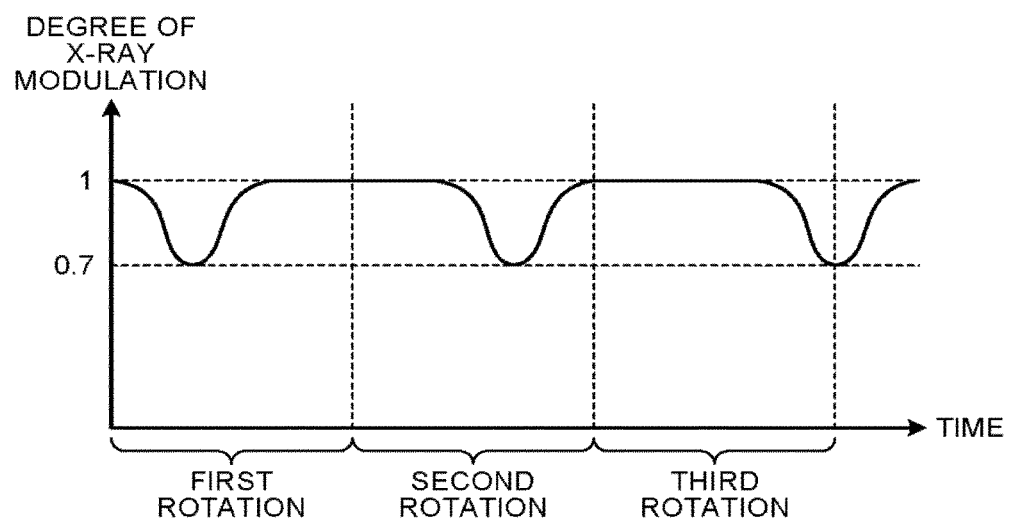
FIG. 9 is a drawing for explaining a reconstructing process performed by an X-ray CT apparatus according to another embodiment.

Further, in the second embodiment above, the example is explained in which the time resolution of the CT images is improved. However, possible embodiments are not limited to this example. For instance, it is also acceptable to try to reduce the dose, instead of improving the time resolution. In that situation, the X-ray CT apparatus further includes an intensity modulating unit. The intensity modulating unit is configured to perform a modulating process so that the X-ray intensity is different for each of the rotations, when rotation imaging processes are continuously performed on a patient in the presence of a contrast agent. In other words, the intensity modulating unit modulates the X-ray intensity in accordance with the angles, when rotation imaging processes are continuously performed on a patient in the presence of a contrast agent. FIG. 9 is a drawing for explaining a reconstructing process performed by an X-ray CT apparatus according to another embodiment. In that situation, X-rays are radiated with an intensity distribution obtained by further applying the modulation distribution illustrated in FIG. 9 to the intensity distribution illustrated in FIG. 8. In this situation, the intensity modulating unit is able to achieve a more advantageous effect by ensuring that the position in which the degree of X-ray modulation is the highest varies for each rotation. In the example illustrated in FIG. 9, the situation where the degree of X-ray modulation is 0.7 corresponds to the position in which the degree of X-ray modulation is the highest. In other words, in the example illustrated in FIG. 9, in the first rotation, the degree of X-ray modulation is the highest when the rotation angle is 120 degrees. In the second rotation, the degree of X-ray modulation is the highest when the rotation angle is 240 degrees. In the third rotation, the degree of X-ray modulation is the highest when the rotation angle is 360 degrees. Although it becomes possible to reduce the X-ray dose amount by modulating the X-ray intensity, it becomes impossible to achieve a desired level of image quality by using the acquired images from only one rotation. However, because the reconstructing process is performed by using the temporal information to that effect, it is possible to prevent the image quality from being degraded, which is inevitable in conventional examples using a reconstruction algorithm. It is also acceptable to configure the X-ray diagnosis apparatus 1 according to the first embodiment so as to further include an intensity modulating unit. In that situation, the intensity modulating unit included in the X-ray diagnosis apparatus 1 according to the first embodiment is configured to modulate the X-ray intensity in accordance with the angles, when rotation imaging processes are continuously performed on a patient in the presence of a contrast agent. Further, the intensity modulating unit included in the X-ray diagnosis apparatus 1 according to the first embodiment may be configured so that the position in which the degree of X-ray modulation is the highest varies for each rotation.

Further, in the first embodiment, the example is explained in which the radiation diagnosis apparatus is the X-ray diagnosis apparatus. In the second embodiment, the example is explained in which the radiation diagnosis apparatus is the X-ray CT apparatus. However, the radiation diagnosis apparatus does not necessarily have to be an X-ray diagnosis apparatus or an X-ray CT apparatus. For example, the radiation diagnosis apparatus may be a nuclear medical imaging apparatus such as a Single Photon Emission Computed Tomography (SPECT) apparatus or a Positron Emission computed Tomography (PET) apparatus. Thus, as another example of the radiation diagnosis apparatus, a SPECT apparatus will be explained.

Figure 10:
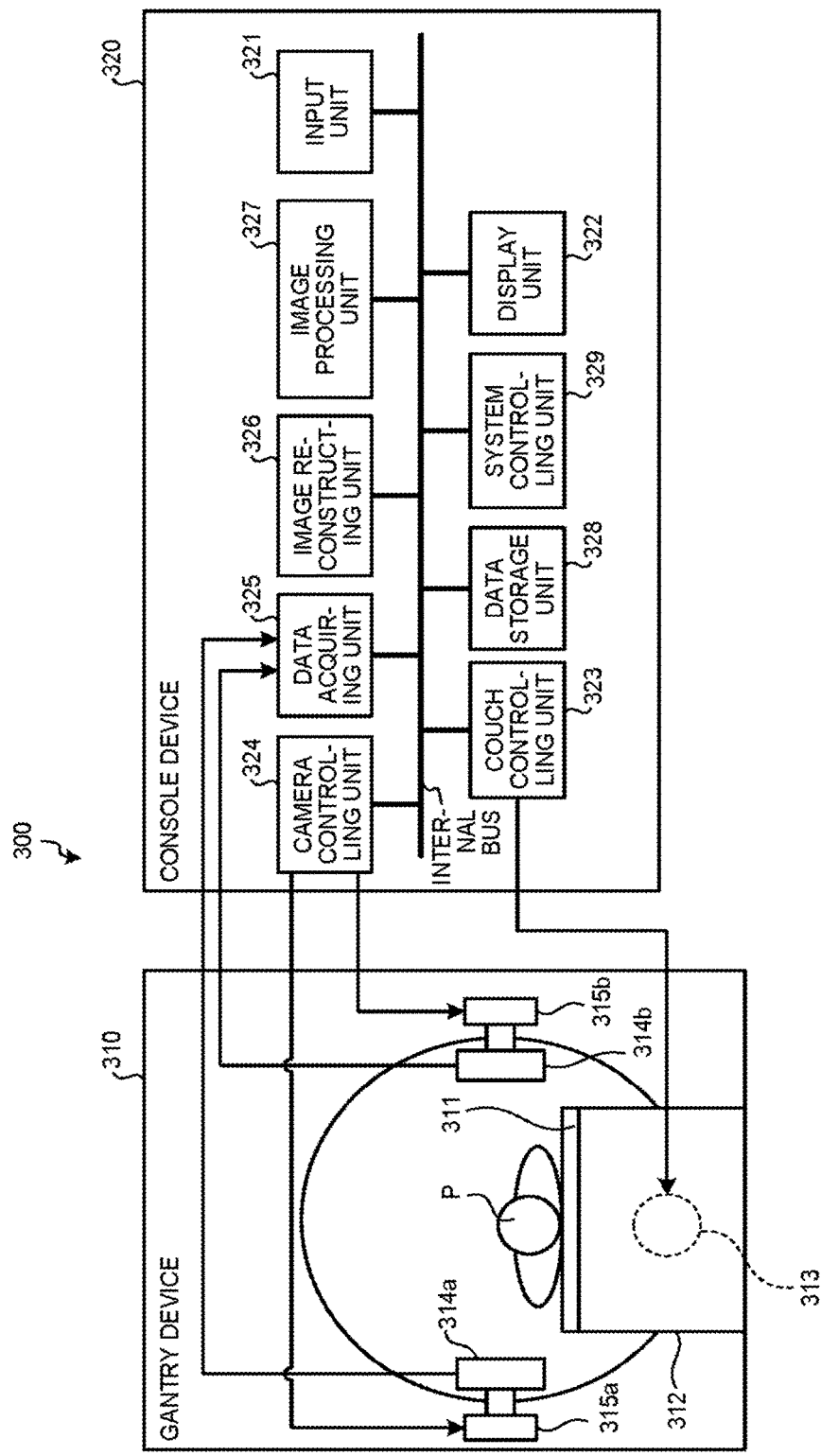
FIG. 10 is a block diagram of an exemplary configuration of a Single Photon Emission Computed Tomography (SPECT) apparatus according to yet another embodiment.

FIG. 10 is a block diagram of an exemplary configuration of a SPECT apparatus according to yet another embodiment. As illustrated in FIG. 10, a SPECT apparatus 300 according to the present embodiment includes a gantry device 310 and a console device 320.

The gantry device 310 is configured to detect radial rays (hereinafter, "gamma rays" as appropriate) emitted from a radioactive medicine (which may be called a radioactive medical agent) that is administered to the patient P and selectively taken into a biological tissue of the patient P and to acquire projection data generated on the basis of the detected radial rays. As illustrated in FIG. 10, the gantry device 310 includes a couchtop 311, a couch 312, and a couch driving unit 313. Further, the gantry device 310 also includes a gamma camera 314a and a camera driving unit 315a, as well as a gamma camera 314b and a camera driving unit 315b. As illustrated in FIG. 10, the gantry device 310 has a hollow space serving as an image taking opening. The gamma camera 314a and the camera driving unit 315a may be referred to as a first imaging system, whereas the gamma camera 314b and the camera driving unit 315b may be referred to as a second imaging system.

The couchtop 311 is a bed on which the patient P lies down and is arranged on the couch 312. The couch driving unit 313 is configured to move the patient P into the image taking opening of the gantry device 310 by moving the couch 312, under control of a couch controlling unit 323 (explained later).

The gamma camera 314a and the gamma camera 314b are each a detector configured to detect the gamma rays emitted from a radioisotope (hereinafter, "RI", as appropriate) of a radioactive medicine administered to the patient P. In other words, the first imaging system and the second imaging system each include a detector capable of detecting the radial rays emitted from the radioactive medicine. The gantry device 310 according to the present embodiment includes the two gamma cameras serving as the detectors configured to detect the gamma rays; however, possible embodiments are not limited to this example. The present disclosure is similarly applicable to situations where the gantry device 310 includes one gamma camera or three or more gamma cameras.

The gamma camera 314a and the gamma camera 314b are each configured to two-dimensionally detect an intensity distribution of the gamma rays emitted from the radioactive medicine. Further, the gamma camera 314a and the gamma camera 314b are each configured to generate projection data by performing, for example, an amplifying process and an Analog/Digital conversion process on the detected intensity distribution data and to transfer the generated projection data to a data acquiring unit 325 (explained later). For example, the gamma camera 314a and the gamma camera 314b may each be a radial ray detector that uses a photon counting method and includes a scintillator and a photomultiplier tube (hereinafter, "PMT" as appropriate). The scintillator is configured to convert the gamma rays into light that has a peak thereof in an ultraviolet region. The PMT is configured to multiply the light emitted from the scintillator and to convert the result into an electric signal. Further, a collimator configured to regulate the incident direction is attached to each of the gamma cameras 314a and 314b. The gamma camera 314a and the gamma camera 314b each detect the gamma rays that have become incident in the incident direction regulated by the collimator.

The camera driving unit 315a and the camera driving unit 315b are each configured to move the gamma camera 314a and the gamma camera 314b, respectively, under the control of a camera controlling unit 324 (explained later). For example, the camera driving unit 315a moves the gamma camera 314a to a predetermined position along the inside of the image taking opening of the gantry device 310. Further, for example, the camera driving unit 315b moves the gamma camera 314b to a predetermined position along the inside of the image taking opening of the gantry device 310. In this manner, the gamma camera 314a and the gamma camera 314b each generate the projection data in the predetermined single direction.

Further, the camera driving unit 315a and the camera driving unit 315b move the gamma camera 314a and the gamma camera 314b, respectively, so as to be positioned apart from each other at a predetermined angle and drive the gamma camera 314a and the gamma camera 314b, respectively, to rotate along the inside of the image taking opening while the distance between the two cameras is maintained. In this manner, the gamma camera 314a and the gamma camera 314b rotate around the patient P and generate the projection data in a plurality of directions among the 360 degrees.

The console device 320 is configured to receive operations performed on the SPECT apparatus 300 and to reconstruct SPECT images from the projection data acquired by the gantry device 310. As illustrated in FIG. 10, the console device 320 includes an input unit 321, a display unit 322, the couch controlling unit 323, the camera controlling unit 324, the data acquiring unit 325, an image reconstructing unit 326, an image processing unit 327, a data storage unit 328, and a system controlling unit 329. These functional units are connected to each other via an internal bus.

The input unit 321 is a mouse, a keyboard, and/or the like used by an operator of the SPECT apparatus to input various types of instructions and various types of settings. Further, the input unit 321 transfers the input instructions and settings to the system controlling unit 329. The display unit 322 is a monitor referenced by the operator. Under the control of the system controlling unit 329, the display unit 322 is configured to display the SPECT images and a Graphical User Interface (GUI) or the like used for receiving the various types of instructions and the various types of settings from the operator via the input unit 321.

The data acquiring unit 325 is configured to acquire the projection data transmitted thereto from each of the gamma cameras 314a and 314b. Further, the data acquiring unit 325 generates post-correction projection data by performing correcting processes such as an offset correcting process, a sensitivity correcting process, and the like on the acquired projection data and stores the generated post-correction projection data into the data storage unit 328. Possible embodiments, however, are not limited to this example. For instance, the gamma camera 314a and the gamma camera 314b may each transmit intensity distribution data to the data acquiring unit 325, so that the data acquiring unit 325 generates projection data from the intensity distribution data and generates post-correction projection data from the generated projection data.

The image reconstructing unit 326 is configured to reconstruct the SPECT images by reading the post-correction projection data from the data storage unit 328 and performing a back projection process on the read post-correction projection data (e.g., post-correction projection data corresponding to directions among the 360 degrees). For example, the image reconstructing unit 326 reconstructs the SPECT images by implementing an iterative reconstruction algorithm. Further, the image reconstructing unit 326 stores the reconstructed SPECT images into the data storage unit 328. The image processing unit 327 is configured to read the SPECT images from the data storage unit 328 and to perform various types of processes on the read SPECT images.

The system controlling unit 329 is configured to exercise overall control of the SPECT apparatus by controlling operations of the gantry device 310 and the console device 320. More specifically, the system controlling unit 329 causes the gantry device 310 to perform the projection data acquiring process, by controlling the couch controlling unit 323 and the camera controlling unit 324. Further, the system controlling unit 329 is configured to control the entirety of the image processing processes performed by the console device 320, by controlling the correcting processes performed by the data acquiring unit 325 and the image generating processes performed by the image reconstructing unit 326 and the image processing unit 327. Furthermore, the system controlling unit 329 is configured to exercise control so that the display unit 322 displays any of the data stored in the data storage unit 328.

In the SPECT apparatus according to the present embodiment configured as described above, for example, the image reconstructing unit 326 reconstructs three-dimensional medical agent distribution images in a time series from the projection data, by performing an iterative reconstruction process that uses at least one selected from between spatial continuity of the medical agent and temporal continuity of the concentration of the medical agent as a constraint condition. In this situation, similarly to the processing procedure illustrated in FIG. 4, the image reconstructing unit 326 performs the iterative reconstruction process by solving Expression (1) presented above. In that situation also, the TV of the f-vector can be expressed as indicated in Expression (2) presented above. In this situation, the spatial constraint condition is based on the notion that the tissue structure in which the radioactive medicine administered to the patient P is distributed does not rapidly change morphologically. The temporal constraint condition is based on the notion that the concentration of the radioactive medicine administered to the patient P does not fluctuate quickly, at mutually the same coordinates in the three-dimensional images. In other words, for example, the SPECT apparatus 300 uses the tissue structure of the patient P to whom the radioactive medicine was administered as the constraint condition based on the spatial continuity of the medical agent. Further, the SPECT apparatus 300 uses the concentration of the ratio active medicine at mutually the same coordinates in the three-dimensional images as the constraint condition based on the temporal continuity of the concentration of the medical agent.

As explained above, because the SPECT apparatus according to the present embodiment performs the iterative reconstruction process by using the constraint condition, it is possible to select an appropriate solution from among innumerable solutions. As a result, the SPECT apparatus according to the present embodiment is able to accurately reconstruct the three-dimensional medical agent distribution images in the time series.

Although the SPECT apparatus was explained with reference to FIG. 10 as an example of nuclear medical imaging apparatuses, possible embodiments are not limited to this example. For instance, the nuclear medical imaging apparatus may be a PET apparatus. In that situation, for example, the PET apparatus is configured to reconstruct three-dimensional medical agent distribution images in a time series from acquired images, by performing a iterative reconstruction process that uses at least one selected from between spatial continuity of the medical agent and temporal continuity of the concentration of the medical agent as a constraint condition.

The constituent elements of the apparatuses and the devices illustrated in the drawings in the description of the embodiment above are based on functional concepts. Thus, it is not necessary to physically configure the constituent elements as indicated in the drawings. In other words, the specific modes of distribution and integration of the apparatuses and the devices are not limited to the ones illustrated in the drawings. It is acceptable to functionally or physically distribute or integrate all or a part of the apparatuses and the devices in any arbitrary units, depending on various loads and the status of use. Further, all or an arbitrary part of the processing functions implemented by the apparatuses and the devices may be realized by a CPU and a computer program analyzed and executed by the CPU or may be realized as hardware using wired logic.

Further, the controlling methods explained in the embodiments above may be realized by causing a controlling computer program (hereinafter, "controlling program") prepared in advance to be executed by a computer such as a personal computer or a workstation. The controlling program may be distributed via a network such as the Internet. Further, the controlling program may be recorded on a computer-recordable recording medium such as a hard disk, a flexible disk (FD), a Compact Disk Read-Only Memory (CD-ROM), a Magneto-Optical (MO) disk, or a Digital Versatile Disk (DVD) and may be executed as being read from the recording medium by a computer.

According to at least one aspect of the embodiments described above, it is possible to accurately reconstruct the three-dimensional images in the time series.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A radiation diagnosis apparatus comprising:
   reconstructing circuitry configured to:
   acquire a group of acquired images acquired in presence of a medical agent by an imaging system from directions in a range that makes it possible to reconstruct three-dimensional images of a subject in a time series;
   reconstruct three-dimensional medical agent distribution images in the time series from the group of acquired images, by performing an iterative reconstruction process while evaluating an error value represented by a difference between a pixel value obtained by projecting an estimated voxel value of a three-dimensional image onto each of a plurality of signal detection planes and a pixel value of each of the acquired images and at least one selected from between spatial continuity of the medical agent and temporal continuity of a concentration of the medical agent.

2. The radiation diagnosis apparatus according to claim 1, wherein
   the imaging system includes an X-ray generator and an X-ray detector,
   the medical agent is a contrast agent, and
   as the three-dimensional medical agent distribution images in the time series, the reconstructing circuitry reconstructs three-dimensional blood vessel images in a time series from a group of acquired images generated from X-ray signals acquired in absence of the contrast agent by the imaging system by performing a rotation imaging process on the subject and a group of acquired images generated from X-ray signals acquired in the presence of the contrast agent by the imaging system by performing a rotation imaging process on the subject, by performing an iterative reconstruction process that uses at least one selected from between spatial continuity of a blood vessel structure of which image contrast is enhanced by the contrast agent and temporal continuity of the medical agent concentration as a constraint condition.

3. The radiation diagnosis apparatus according to claim 2, wherein
the imaging system is a bi-plane type imaging system including two sets each made up of the X-ray generator and the X-ray detector, and
the reconstructing circuitry reconstructs the three-dimensional blood vessel images from the groups of acquired images acquired by the bi-plane type imaging system by performing the rotation imaging processes.

4. The radiation diagnosis apparatus according to claim 2, further comprising:
difference image generating circuitry configured to generate a group of difference images from the group of acquired images generated from the X-ray signals acquired in the absence of the contrast agent by performing the rotation imaging process on the subject and the group of acquired images generated from the X-ray signals acquired in the presence of the contrast agent by performing the rotation imaging process on the subject, wherein
the reconstructing circuitry reconstructs the three-dimensional blood vessel images in the time series from the group of difference images.

5. The radiation diagnosis apparatus according to claim 4, wherein the reconstructing circuitry reconstructs the three-dimensional blood vessel images in the time series from a group of difference images generated at predetermined time intervals that are among the group of difference images sequentially generated during a time period of the rotation imaging processes.

6. The radiation diagnosis apparatus according to claim 4, wherein, during the iterative reconstruction process, the reconstructing circuitry calculates the error value by adding the constraint condition to a difference between a pixel value obtained by projecting an estimated voxel value of a three-dimensional image onto each of a plurality of X-ray signal detection planes and a pixel value of each of the difference images and repeatedly performs the reconstructing process until the error value becomes equal to or smaller than a predetermined threshold value.

7. The radiation diagnosis apparatus according to claim 4, wherein the reconstructing circuitry reconstructs the three-dimensional blood vessel images in the time series from the group of difference images, by performing the iterative reconstruction process that uses the constraint condition, in a region of interest that is set.

8. The radiation diagnosis apparatus according to claim 2, further comprising: blood flow information generating circuitry configured to generate blood flow information by analyzing the reconstructed three-dimensional blood vessel images in the time series.

9. The radiation diagnosis apparatus according to claim 2, further comprising: intensity modulating circuitry configured to modulate an X-ray intensity in accordance with angles, when the rotation imaging process is continuously performed on the subject in the presence of the contrast agent.

10. The radiation diagnosis apparatus according to claim 2, wherein the group of acquired images is acquired while the contrast agent is reaching a capillary phase.

11. The radiation diagnosis apparatus according to claim 1, wherein the radiation diagnosis apparatus is an X-ray CT apparatus.

12. The radiation diagnosis apparatus according to claim 11, wherein the X-ray CT apparatus is a dual-source type X-ray CT apparatus including a first imaging system and a second imaging system.

13. The radiation diagnosis apparatus according to claim 1, wherein
the medical agent is a radioactive medical agent, and
the imaging system includes a detector configured to be capable of detecting radial rays emitted from the radioactive medical agent.

14. The radiation diagnosis apparatus according to claim 1, wherein the radiation diagnosis apparatus is a SPECT apparatus.

15. The radiation diagnosis apparatus according to claim 1, wherein the radiation diagnosis apparatus is a PET apparatus.

16. The radiation diagnosis apparatus according to claim 1, wherein the imaging system acquires the group of acquired images from the directions that form an angle equal to or larger than 180 degrees with respect to the subject.

* * * * *